United States Patent [19]

Telschow

[11] Patent Number: 4,560,773
[45] Date of Patent: Dec. 24, 1985

[54] PROCESS FOR PREPARING SUBSTITUTED PHTHALIC ANHYDRIDES

[75] Inventor: Jeffrey E. Telschow, Tarrytown, N.Y.

[73] Assignee: Stauffer Chemical Company, Westport, Conn.

[21] Appl. No.: 600,247

[22] Filed: Apr. 16, 1984

[51] Int. Cl.$^4$ ............................................. C07D 307/89
[52] U.S. Cl. ..................................... 549/240; 549/247
[58] Field of Search .......................................... 549/240

[56] References Cited

U.S. PATENT DOCUMENTS 2,097,854 11/1937 Dilthey ................................ 549/240
2,264,429 12/1941 Bergmann ........................ 549/240 X
2,391,226 12/1945 Clifford et al. ...................... 549/240

OTHER PUBLICATIONS

Craig, JACS, vol. 72 (1950), pp. 3732 & 3733.
Newman et al., JACS, vol. 63 (1941), pp. 1542–1544.
Izv. Akad. Nauk. SSSR, Serkhim, vol. 6 (1973), p. 1315.

Primary Examiner—Richard L. Raymond
Attorney, Agent, or Firm—Hensley M. Flash

[57] ABSTRACT

A process for preparing substituted phthalic anhydrides, e.g. 4-methylphthalic anhydride, in which the Diels-Alder addition product of a conjugated diene, e.g. isoprene, and maleic anhydride is reacted with bromine in the presence of a catalytic quantity of an acid acceptor. Typical catalytic acid acceptors include dimethylformamide and pyridine.

19 Claims, No Drawings

PROCESS FOR PREPARING SUBSTITUTED PHTHALIC ANHYDRIDES

BACKGROUND OF THE INVENTION

1. Field of the Invention

This invention relates to a process for preparing substituted phthalic anhydrides. More particularly, it relates to a process for preparing 4-methyl phthalic anhydride.

2. Related Art

Phthalic anhydrides are valuable raw materials for making various useful products. These anhydrides are useful as intermediates in the chemical synthesis of herbicides and particularly in the synthesis of certain herbicides used to protect cereal crops. Other uses for these raw materials include polycyclic dyes, alkyd and epoxy resins, polyesters and plasticizers.

U.S. Pat. No. 2,391,226 (Clifford et al., Dec. 18, 1945) discloses addition products of chlormaleic anhydride and dichlormaleic anhydride prepared by the Diels-Alder reaction and the dehydrochlorination of these products in the presence of a catalyst, such as a secondary or tertiary amine. However, the six-carbon ring is usually only partially dehydrogenated yielding a substituted dihydrophthalic anhydride.

U.S. Pat. No. 2,264,429 (Bergman, Dec. 2, 1941) discloses a process for preparing substituted phthalic anhydride in a single reaction. This reaction involves the combination of the condensation reaction between a diene and maleic anhydride and the dehydrogenation reaction. This combination is achieved by carrying out the condensation reaction in nitrobenzene or another nitrated aromatic substance which not only acts as a diluent, but also as a dehydrogenating agent by reducing itself and giving the corresponding amine. This patent discloses o-nitrotoluene as another example of a nitrated aromatic substance useful in the disclosed process.

SUMMARY OF THE INVENTION

A process for preparing substituted phthalic anhydrides in good yields would be advantageous because of the various useful products that are prepared from these anhydrides. It is an object of the present invention to provide a unique, cost effective process for the preparation of substituted phthalic anhydrides. Other objects and advantages of the present invention are shown throughout the specification.

In accordance with the present invention, it has now been discovered that substituted phthalic anhydrides can be prepared by a process which comprises reacting the Diels-Alder addition product of a conjugated diene and maleic anhydride with bromine in the presence of a catalytic amount of an acid acceptor.

DETAILED DESCRIPTION OF THE INVENTION

The present invention comprises a process for preparing substituted phthalic anhydrides by reacting the Diels-Alder addition product of a conjugated diene and maleic anhydride with bromine in the presence of a catalytic amount of an acid acceptor.

The substituted phthalic anhydrides of this invention can include a substituent or the lack of a substituent at each of the four available sites on the benzene ring, i.e. the 3,4,5 and 6 carbon positions. These substituents can be selected from the group consisting of $C_1$ to $C_{10}$ alkyl, $C_6$ to $C_{14}$ aryl and $C_1$ to $C_{16}$ aralkyl and wherein the alkyl, aryl and aralkyl are optionally substituted with halogens, nitro groups, cyano groups and carboxylic groups.

The process can use the Diels-Alder addition product as a starting material or can comprise a first step of actually preparing this addition product. The Diels-Alder addition product can be derived from other than the Diels-Alder reaction. In addition, the double bond isomers of the Diels-Alder addition product can be used in the process of this invention.

The Diels-Alder addition products of this invention are formed by reacting maleic anhydride with a conjugated diene. The conjugated diene can include butadiene, 2,3-dimethylbutadiene, other substituted butadienes and preferably isoprene.

The addition product can be prepared by reacting the maleic anhydride with the conjugated diene in a nitrogen atmosphere. The maleic anhydride is usually heated until it melts, then the conjugated diene is added slowly under the surface of the melt. When the addition of the diene is completed, the reactants can then be heated up to a reaction temperature of from about 55° C. up to about 120° C. with temperatures in the upper end of the range from about 100° C. up to about 120° C. being preferred. The reactants are kept within the reaction temperature range until the reaction is completed, usually for about 1 hour. The reaction can be exothermic, therefore external cooling can be required to maintain the reactants within the reaction temperature range.

After the reaction to form the addition product is completed, excess diene can be stripped from the reaction zone under vacuum at a pressure which will minimize sublimation of the addition product. This reaction can take place in the presence of an appropriate solvent, however the absence of a solvent is preferred for the process of this invention.

The stoichiometry of this Diels-Alder addition reaction usually involves one mole of the maleic anhydride reacting with one mole of the conjugated diene to produce one mole of the addition product, therefore it is economically desirable to react equimolar quantities of the reactants. However, a fractional molar excess of the diene is usually used to ensure that all the maleic anhydride is consumed in the reaction.

When the Diels-Alder addition product is used as a starting material, the following procedure can be used in accordance with this invention. The addition product is heated in a reactor having a nitrogen atmosphere until it melts. The acid acceptor catalyst is first added to the melt, then the temperature is raised to about 120° C. Bromine can then be added slowly to the reactor under the surface of the melt. After the bromine addition begins, hydrogen bromide will slowly begin to evolve, then increase to a fairly constant rate. The bromine addition can be adjusted to such a rate that none of the characteristic bromine color is evident within the liberated hydrogen bromide. The bromine addition can be mildly to moderately exothermic. During the bromine addition, the temperature in the reaction zone is maintained at from about 100° C. up to about 180° C. with from about 135° C. up to about 145° C. being preferred.

After the bromine addition is completed, the temperature within the reaction zone can be slowly increased up to about 180° C. to ensure completion of the reaction. This is evidenced by the cessation of hydrogen bromide evolution. A bubbler containing mineral oil in the exit line can be used to monitor hydrogen bromide evolution.

A crude melt remains within the reactor after the reaction is completed. This melt can be distilled directly, without an aqueous work-up, to produce a high purity substituted phthalic anhydride.

This process can take place in the presence of an appropriate solvent, however the absence of a solvent is preferred. When a solvent is used an aqueous work-up can be required as an additional purification step, especially if the solvent reacts with hydrogen bromide.

The acid acceptors that can be used in this process as catalysts are varied, however pyridine and dimethylformamide are preferred, with DMF being most preferred. When DMF is the catalyst used, its residue can remain within the reactor with the residue that remains after the distillation of the substituted phthalic anhydride end product, whereas this may not be the case when pyridine is used as the catalyst.

The reaction can occur without a catalyst, however the reaction rate and the purity and yield of the desired end product would be lower than when a catalyst is used. The concentration of the acid acceptor used in this process as a catalyst can range from about 0.1 to 10.0 weight percent with a range from about 1.0 to 5.0 weight percent being preferred. These weight percents are based on the weight of the Diels-Alder addition product used in the reaction.

In a preferred embodiment of this invention, 4-methylphthalic anhydride, (4-MPA), is prepared. This process comprises reacting 4-methyl-1,2,3,6-tetrahydrophthalic anhydride, (4-MTPA), with bromine in the presence of a catalytic amount of an acid acceptor. The acid acceptors used as a catalyst can be dimethylformamide, (DMF), or pyridine with DMF being most preferred. This process can be carried out in the presence of an appropriate solvent, however the absence of a solvent is preferred. The 4-MPA resulting from this process can be distilled directly from the reaction zone without the need for an aqueous work-up or other solvent extraction step.

In another preferred embodiment 4-MPA can be prepared by a process which comprises a first step of reacting isoprene and maleic anhydride to form the Diels-Alder addition product, 4-MTPA, then proceeding to react the 4-MTPA with bromine in the presence of a catalytic amount of an acid acceptor as described above.

The following Examples describe various embodiments of the invention. Other embodiments will be apparent to the skilled in the art from a consideration of this specification or practice of the invention disclosed herein. It is intended that the specifications and Examples be considered as exemplary only, with the true scope and spirit of the invention being indicated by the claims which follow the Examples.

EXAMPLE 1

In a 1 liter 3-necked flask fitted with a dropping funnel, a mechanical stirrer, a pot thermometer and condenser was placed 98.1 gms (1.0 mole) of maleic anhydride. The flask was heated in an oil bath until the maleic anhydride melted. Isoprene (69.5 gms, 1.02 moles) was then added dropwise to the flask below the surface of the maleic anhydride melt, using an extension tube of TEFLON fluorocarbon polymer attached to the dropping funnel, at such a rate as to minimize the reflux. The temperature of the reactants in the flask was controlled with intermittent cooling and kept between 55° C. to 100° C.

After the addition of the isoprene was completed, the reactor flask was heated to 120° C. and maintained at that temperature for 60 minutes to ensure complete reaction. Excess isoprene was then stripped from the reactor at 100 mm/90° C. for 20 minutes.

The faintly yellow, molten 4-methyl-1,2,3,6-tetrahydrophthalic anhydride (4-MTPA, mp 58° C.-63° C.) remained in the reactor flask.

EXAMPLE 2

The following example represents a generalized procedure.

Molten 4-MTPA (166.1 gms, 1.0 mole) was prepared in a 3-necked flask without solvent as described above in Example 1. Dimethylformamide (DMF, 5.0 gms, 0.068 moles) was added to the flask.

The content of the flask was then heated to 120° C. and stirred mechanically while bromine (103.5 mls, 322.8 gms, 2.02 moles) was added dropwise under the surface of the melt. The reactor temperature increased to approximately 140° C. and was maintained at between 135° C. to 145° C. throughout the 2.5 to 3.5 hours bromine addition by means of an oil bath thermostatically controlled at 140° C. to 145° C. Hydrogen bromide began to evolve a few minutes after the bromine addition began and was neutralized in a trap containing a sodium hydroxide solution. The bromine addition rate was adjusted so that no bromine color was observed in the hydrogen bromide liberated.

After the addition of the bromine was completed, the dark brown melt was maintained at 140° C. for 15 minutes, then slowly heated to 180° C. to complete the liberation of hydrogen bromide. After 1 hour at 180° C., the crude brown melt remaining was distilled from the flask using a 3" Vigreaux column and a short, uncooled condenser. The pale yellow distillate was collected quickly at bp 153° C.-157° C./7 mm. After cooling, a pale yellow to white solid product, 4-methylphthalic anhydride (4-MPA), resulted. The 4-MPA weighed between 124-130 g (76%-80% yield), with a melting point of 78° C.-89° C., and an assay by hplc of 95% purity.

EXAMPLE 3

Molten 4-MTPA (166.1 gms, 1.0 mole) was prepared as described in Example 1. Pyridine (8.5 ml, 8.3 gms, 0.105 mole) was added to the flask.

The mechanically stirred contents of the flask were maintained at 105° C.-120° C. as bromine (103.5 ml, 322.8 gms, 2.02 moles) was added dropwise under the surface of the melt over 3.5 hrs. Hydrogen bromide evolved continuously. After the addition was completed, the reactor flask temperature was maintained at 110° C. for 2 hrs. Gc analysis showed that the reaction was incomplete, so another 10 mls of bromine was added at 110° C.-120° C. over 40 min. The dark brown melt was then heated to 150° C.-155° C. for 4 hrs to complete the liberation of hydrogen bromide.

The crude melt was distilled under vacuum as in Example 2. After a small forerun, the main fraction was collected at bp 129° C.-131° C./1.5mm. The white solid, 4-MPA, obtained on cooling weighed 110.7 gms (62% yield) and was 90% pure by hplc assay.

What is claimed is:

1. A process for preparing a substituted phthalic anhydride which comprises reacting the Diels-Alder addition product of a conjugated diene and maleic anhydride with bromine in the presence of a catalytic amount of an acid acceptor.

2. The process of claim 1 wherein said conjugated diene is isoprene.

3. The process of claim 1 wherein the acid acceptor is dimethylformamide.

4. The process of claim 1 wherein the acid acceptor is pyridine.

5. A process for preparing 4-methylphthalic anhydride which comprises reacting 4-methyl-1,2,3,6-tetrahydrophthalic anhydride with bromine in the presence of a catalytic amount of an acid acceptor.

6. The process of claim 5 wherein the acid acceptor is dimethylformamide.

7. The process of claim 5 wherein the acid acceptor is pyridine.

8. The process of claim 1 wherein the reaction is carried out in the absence of a solvent.

9. The process of claim 8 wherein the substituted phthalic anhydride is distilled directly.

10. A process for preparing a substituted phthalic anhydride which comprises:
(a) reacting a conjugated diene and maleic anhydride to form a Diels-Alder addition product;
(b) reacting the addition product with bromine in the presence of a catalytic amount of an acid acceptor.

11. The process of claim 10 wherein step (a) and (b) are carried out in the absence of a solvent.

12. The process of claim 11 wherein the substituted phthalic anhydride is distilled directly.

13. The process of claim 10 wherein the acid acceptor is dimethylformamide.

14. The process of claim 10 wherein the acid acceptor is pyridine.

15. A process for preparing 4-methylphthalic anhydride which comprises:
(a) reacting isoprene and maleic anhydride to form 4-methyl-1,2,3,6-tetrahydrophthalic anhydride;
(b) reacting the 4-methyl-1,2,3,6-tetrahydrophthalic anhydride with bromine in the presence of a catalytic amount of an acid acceptor.

16. The process of claim 15 wherein the acid acceptor is dimethylformamide.

17. The process of claim 15 wherein the acid acceptor is pyridine.

18. The process of claim 15 wherein step (a) and (b) are carried out in the absence of a solvent.

19. The process of claim 18 wherein the 4-methylphthalic anhydride is distilled directly.

* * * * *